| (12) | United States Patent | (10) Patent No.: US 12,062,168 B2 |
|---|---|---|
| | Meister et al. | (45) Date of Patent: Aug. 13, 2024 |

(54) REAL-TIME ESTIMATION OF LOCAL CARDIAC TISSUE PROPERTIES AND UNCERTAINTIES BASED ON IMAGING AND ELECTRO-ANATOMICAL MAPS

(71) Applicant: SIEMENS HEALTHINEERS AG, Forchheim (DE)

(72) Inventors: Felix Meister, Erlangen (DE); Tiziano Passerini, Plainsboro, NJ (US); Tommaso Mansi, Plainsboro, NJ (US); Eric Lluch Alvarez, Nuremberg (DE); Chloé Audigier, Bern (CH); Viorel Mihalef, North Brunswick, NJ (US)

(73) Assignee: Siemens Healthineers AG, Forchheim (DE)

(*) Notice: Subject to any disclaimer, the term of this patent is extended or adjusted under 35 U.S.C. 154(b) by 426 days.

(21) Appl. No.: 17/305,631

(22) Filed: Jul. 12, 2021

(65) Prior Publication Data

US 2022/0020145 A1 Jan. 20, 2022

Related U.S. Application Data

(60) Provisional application No. 63/053,849, filed on Jul. 20, 2020.

(51) Int. Cl.
| G06T 7/00 | (2017.01) |
| A61B 6/00 | (2024.01) |
| G06F 18/22 | (2023.01) |
| G06F 18/231 | (2023.01) |
| G06F 18/243 | (2023.01) |

(Continued)

(52) U.S. Cl.
CPC .......... *G06T 7/0012* (2013.01); *A61B 6/5217* (2013.01); *G06F 18/22* (2023.01); *G06F 18/231* (2023.01); *G06F 18/24323* (2023.01); *G06T 7/11* (2017.01); *A61B 6/50* (2013.01); *G06T 2207/20076* (2013.01); *G06T 2207/30061* (2013.01); *G06V 2201/03* (2022.01)

(58) Field of Classification Search
CPC ... G06T 7/0012; G06T 7/11; G06F 18/24323; G06F 18/22; G06F 18/231; A61B 6/5217
See application file for complete search history.

(56) References Cited

U.S. PATENT DOCUMENTS

| 10,342,620 B2 | 7/2019 | Kiraly et al. |
| 10,354,758 B2 | 7/2019 | Yang et al. |
| 11,445,994 B2 * | 9/2022 | Mansi .................. G06T 7/0012 |

(Continued)

OTHER PUBLICATIONS

Stevenson et al., "Catheter Ablation for Ventricular Tachycardia," 2007, Circulation, vol. 115, No. 21, pp. 2750-2760.

(Continued)

*Primary Examiner* — David Bilodeau

(57) ABSTRACT

Systems and methods for estimating local conductivities from anatomical information derived from MR images, ECG, and sparse contact maps are provided. ECG features and sparse measurements are mapped to an anatomical model represented as a graph. Graph convolutional layers and a multilayer perceptron are applied to extract local and global features respectively. The local and global features are combined and further processed by a series of fully connected layers to regress a set of vertex conductivities.

9 Claims, 5 Drawing Sheets

(51) Int. Cl.
*G06T 7/11* (2017.01)
*A61B 6/50* (2024.01)

(56) References Cited

U.S. PATENT DOCUMENTS

| | | | | |
|---|---|---|---|---|
| 2009/0310842 | A1* | 12/2009 | Groth | G06T 7/0012 |
| | | | | 382/128 |
| 2016/0058520 | A1* | 3/2016 | Yang | A61B 34/10 |
| | | | | 703/11 |
| 2017/0103527 | A1* | 4/2017 | Steghöfer | G06T 7/11 |
| 2019/0333643 | A1* | 10/2019 | Villongco | A61B 5/319 |
| 2021/0052252 | A1* | 2/2021 | Hare, II | G06T 7/11 |
| 2021/0090215 | A1* | 3/2021 | Ben-Haim | G06T 7/55 |
| 2021/0183514 | A1* | 6/2021 | Muehlberg | G06T 7/0016 |
| 2021/0287362 | A1* | 9/2021 | Zheng | G06T 7/97 |
| 2021/0334963 | A1* | 10/2021 | Isgum | G16H 50/50 |

OTHER PUBLICATIONS

Prakosa et al., "Personalized virtual-heart technology for guiding the ablation of infarct-related ventricular tachycardia," 2018, Nature Biomedical Engineering, vol. 2, pp. 732-740.

Liang et al., "Long-term Outcomes of Ventricular Tachycardia Ablation in Different Types of Structural Heart Disease," 2015, Arrhythm Electrophysiol Rev., vol. 4, No. 3, pp. 177-183.

Tilz et al., "Ablation Outcomes and Predictors of Mortality Following Catheter Ablation for Ventricular Tachycardia: Data From the German Multicenter Ablation Registry," 2018, Journal of the American Heart Association, vol. 7, No. 6, 14 pgs.

Mansi et al., "Artificial Intelligence for Computational Modeling of the Heart," 2019, Academic Press, 266 pgs.

Dhamala et al., "Bayesian Optimization on Large Graphs via a Graph Convolutional Generative Model: Application in Cardiac Model Personalization," 2019, Medical Image Computing and Computer Assisted Intervention—MICCAI 2019, pp. 458-467.

Pheiffer et al., "Estimation of Local Conduction Velocity from Myocardium Activation Time: Application to Cardiac Resynchronization Therapy," 2017, Functional Imaging and Modelling of the Heart, pp. 239-248.

Neumann et al., "Robust Image-Based Estimation of Cardiac Tissue Parameters and Their Uncertainty from Noisy Data," 2014, Medical Image Computing and Computer-Assisted Intervention—MICCAI 2014, pp. 9-16.

Frangi et al., "Automatic construction of multiple-object three-dimensional statistical shape models: application to cardiac modeling," 2002, IEEE Transactions on Medical Imaging, vol. 21, Issue: 9, pp. 1151-1166.

Hamilton et al., "Inductive Representation Learning on Large Graphs," 2018, 31st Conference on Neural Information Processing Systems (NIPS 2017), 11 pgs.

\* cited by examiner

REAL-TIME ESTIMATION OF LOCAL CARDIAC TISSUE PROPERTIES AND UNCERTAINTIES BASED ON IMAGING AND ELECTRO-ANATOMICAL MAPS

This application claims the benefit of U.S. Provisional Application No. 63/053,849, filed Jul. 20, 2020, the disclosure of which is herein incorporated by reference in its entirety.

TECHNICAL FIELD

The present invention relates generally to estimation of local cardiac tissue properties and uncertainties, and in particular to real-time estimation of local cardiac tissue properties and uncertainties based on imaging and electro-anatomical maps.

BACKGROUND

Catheter-based ablation plays a crucial part in the prevention and reduction of ventricular tachycardias, which can result in sudden cardiac death if left without treatment. Identifying the location of wave re-entry is critical for the success of ablation therapy.

The current standard-of-care to identify the slow pathways causing the wave re-entry is electroanatomical contact mapping. The electroanatomical contact mappings, however, only provide insight into the electrical behavior of the endocardial surface and only at sparse spatial positions, which may result in not identifying the critical pathways. Additional limitations include registrations errors and inability to map the complex 3D pathways inside the myocardium.

In another approach, personalized computational models of cardiac electrophysiology could assist a physician in his or her decision making and guide the intervention. During the intervention, sparse measurements of the patient's electrical activity are acquired and the computational model is updated. However, such computational models require significant and time-consuming manual interaction to generate a personalized physiological model of the heart.

BRIEF SUMMARY OF THE INVENTION

Embodiments described herein are directed to estimating the parameters of a computational model of heart electrophysiology, given a representation of the anatomy of the heart and sparse measurements of its electrical activity, to generate a personalized computational model.

These and other advantages of the invention will be apparent to those of ordinary skill in the art by reference to the following detailed description and the accompanying drawings.

DETAILED DESCRIPTION

The present invention generally relates to real-time estimation of local cardiac tissue properties and uncertainties based on imaging and electro-anatomical maps Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments described herein are directed to estimating the parameters of a computational model of heart electrophysiology, given a representation of the anatomy of the heart and sparse measurements of its electrical activity, to generate a personalized computational model. In particular, embodiments described herein generate a personalized computational model of the heart electrophysiological based on medical imaging data (e.g., MRI (magnetic resonance imaging), CT (computed tomography), US (ultrasound), a sparse left-endocardial contact map of the patient, and ECG (electrocardiogram) data.

Embodiments described herein are based on a neural network trained on a large database of synthetically generated examples. The neural network is applied to data acquired during cardiac interventions to compute the model parameters in real time. The neural network is also trained to output the variance of the target local activation time with respect to similar input features obtained from the training data.

Figure 1:
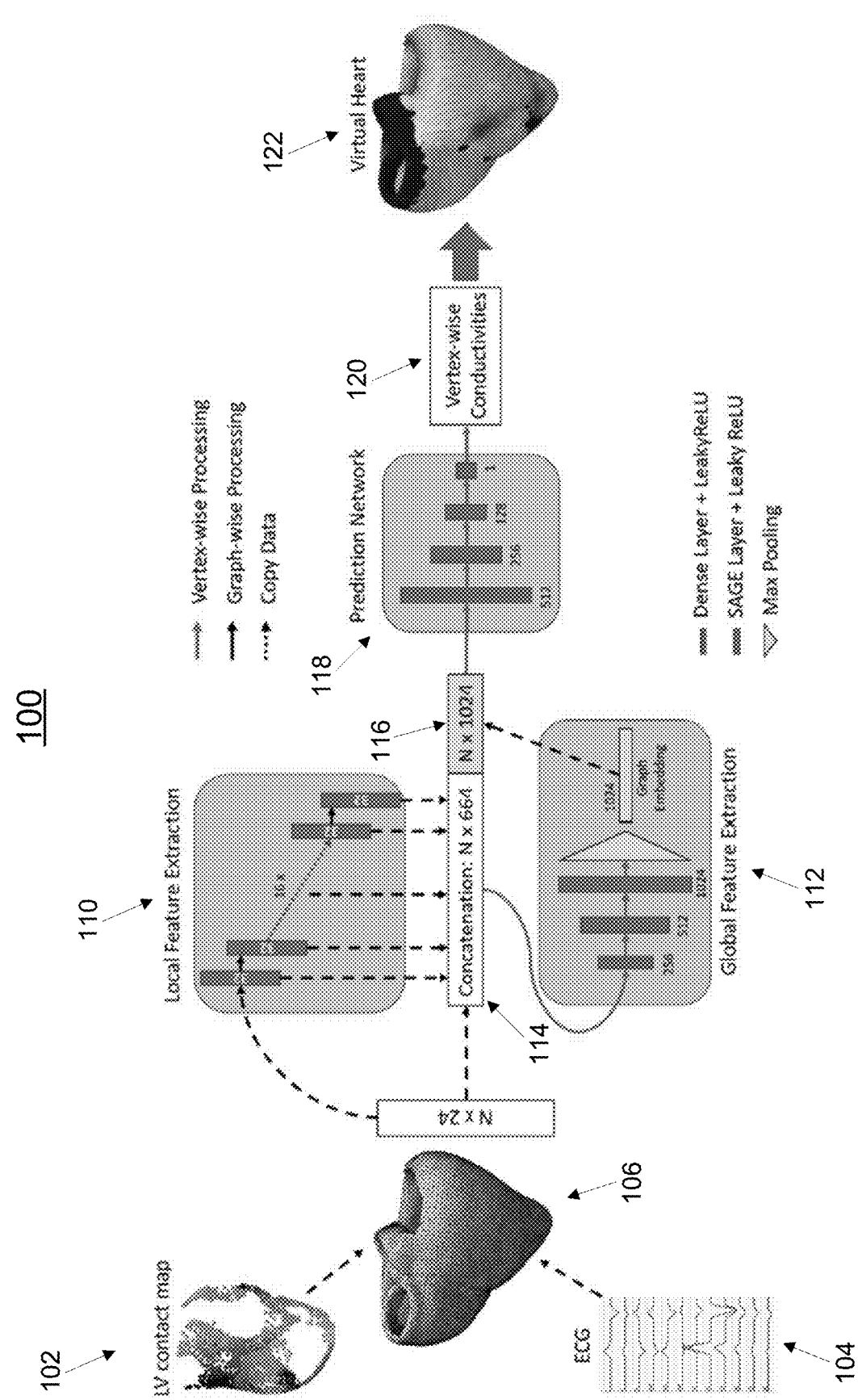
FIG. 1 shows a workflow for estimating local conductivities from anatomical information derived from MR (magnetic resonance) images, ECG (electrocardiogram), and sparse contact maps, in accordance with one or more embodiments.
Figure 2:
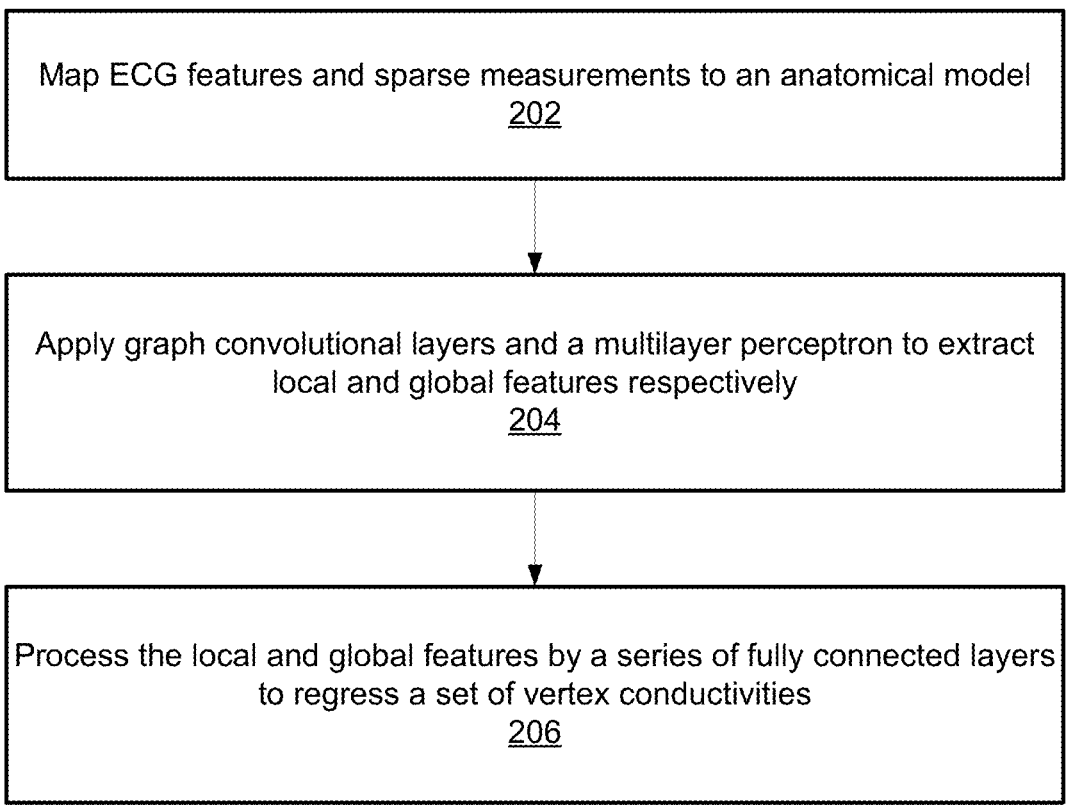
FIG. 2 shows a method for estimating local conductivities from anatomical information derived from MR images, ECG, and sparse contact maps, in accordance with one or more embodiments.

FIG. 1 shows a workflow 100 for estimating local conductivities from anatomical information derived from MR (magnetic resonance) images, ECG (electrocardiogram), and sparse contact maps, in accordance with one or more embodiments. FIG. 2 shows a method 200 for estimating local conductivities from anatomical information derived from MR images, ECG, and sparse contact maps, in accordance with one or more embodiments.

At step 202 of FIG. 2, ECG features and sparse measurements are mapped to an anatomical model. For example, as shown in FIG. 1, ECG features 104 and sparse measurements 102 are mapped to anatomical model 106 represented as a graph.

In one embodiment, the anatomy is approximated as a tetrahedral mesh, i.e., a graph, of a heart, whereas edges and vertices of the graph are assigned one or more features. For instance, vertex features include activation times derived from the computed depolarization; QRS duration, electrical axis, and the lead positivity derived from the ECG traces; and geometric features such as a regional categorical information, distances within the heart (e.g., the distance within apex to base or left ventricle to right ventricle), and a coordinate within an implicit coordinate system built from angle, radius, and height; edge features include the edge distance. In an advantageous embodiment, only a subset of the graph vertices has a non-null value for the feature representing activation time. This is intended as a way to represent the case in which some sparse measurements are available for the left ventricular endocardium, as obtained for instance through electro-anatomical mapping.

In another embodiment, part of the vertices belonging to the mesh representation of the anatomical model are excluded from the graph, so effectively the neural network is only applied to a sub-region of the anatomical model. This could be the case for instance of the presence of an ischemic lesion in the myocardium (scar). A scar can be identified from medical images (e.g., DE-MRI (delayed enhancement MRI)) and the portion of the anatomical model corresponding to the physical location of the scar can be completely excluded from application of the neural network, under the assumption that no electrical activity is taking place there. This has the advantage of improving accuracy of the network, since during the training stage only graph vertices with non-trivial target values (e.g., non-zero conduction velocity) are presented.

At step 204 of FIG. 2, graph convolutional layers and a multilayer perceptron are applied to extract local and global features respectively. For example, as shown in FIG. 1, a local feature extraction network 110 and a global feature extraction network 112 are applied to extract local features 114 and global features 116 respectively from anatomical model 106.

A graph convolutional neural network is trained on this dataset to regress the local conduction velocities associated with the given input of anatomy, ECG, and sparse endocardial activation map. Graph convolutions hereby allow to learn filters that act on the local neighborhood of the vertices of the underlying graph. A cascade of graph convolutional layers construct efficient node and graph embeddings, which allow the propagation of information throughout the graph and the regression of functions on the graph based on it.

At step 206 of FIG. 2, the local and global features are combined and further processed by a series of fully connected layers to regress a set of vertex conductivities. For example, as shown in FIG. 1, prediction network 110 generates vertex-wise conductivities 120 from a concatenation of local features 114 and global features 116. These conductivities can be incorporated in a virtual heart 122 to compute the depolarization.

The target value in FIG. 1 is the target value is the conduction velocity at each node for each generated electrophysiological state defined as the combination of a given anatomical model and a simulated electrical activity. The conduction velocity may be used in the cardiac electrophysiology model to compute electrical activity. However, the target values to be regressed by the network may be any physical parameters or property of the heart as represented by the cardiac electrophysiology model, including for instance, any of the parameters describing cellular electrophysiology (e.g. action potential duration). In another embodiment, the local activation time as computed by the electrophysiology model is used as target value.

The neural network implementing prediction network 110 is trained on a large database of synthetically generated examples. The large database of examples may comprise heart geometries and sparse electrical activity measurements. In one embodiment, multiple heart anatomies are synthetically generated by a rule-based approach. By this approach, the heart anatomy is approximated by a parametric model parameterized for instance by a set of parameters including radius, length, thickness of each chamber; mutual position of the center of each chamber; orientation of the major axis of each chamber; etc. One heart anatomy is uniquely determined by a set of parameters; therefore, a database of heart anatomies is obtained by stochastically varying all parameters within pre-determined value ranges. Value ranges can be determined for instance based on literature or population averages. In an alternative embodiment, a family of heart anatomies can be obtained by means of a statistical shape model built from existing examples (e.g. from segmentation of medical images). Given an anatomical model, electrical activation can be simulated by means of a computational model of cardiac electrophysiology. For each anatomical model, the cardiac electrophysiology model is used to generate a large set of sparse measurements of electrical activity corresponding to plausible electrophysiological states. For instance, by varying one or more of the model parameters such as the local conduction velocity, different values for the local electrical activation are computed for each heart anatomy. In particular, a sparse sample of the computed activation times on the heart endocardium is extracted by randomly sampling the endocardial points. This step approximates the sparse measurements that would be available in a cardiac intervention as electro-anatomical mapping data.

Since the neural network is trained on a large set of physiologically plausible examples produced by the computational model, it implicitly learns to discard solutions that are incompatible with the underlying electrophysiology model. In particular, the network can be trained to be robust to uncertainty in the position of the sparse endocardial measurements of electrical activity by using smart augmentation strategies. In one embodiment, multiple training examples are added to the database by considering for the same anatomical model and same computed electrical activation multiple random samplings of the endocardial activation times. By introducing the network to repeatedly changing random sub-samplings of the endocardial activation and keeping the same target, the network learns to cope with the uncertainty of spatial sampling, thus becoming robust against it.

In another embodiment, the network can be trained to be robust to random perturbation of the sparse endocardial measurements. For instance, a random low-intensity noise can be applied to one or more of the activation time values provided as input features to endocardial vertices of the graph, while always showing as ground truth to the network the same target values computed by the cardiac electrophysiology model (in absence of noise). This will force the network to learn to provide robust prediction in presence of low intensity noise in the endocardial measurements. Following the same approach, the noise could be applied to the location of the measurement, rather than to its value. For instance, given a set of endocardial points with measurements, application of a low intensity noise to their location could be obtained by randomly associating each point's original measurement to a different vertex in a neighborhood of given radius (e.g., a 1-hop neighborhood). This would teach the network to be robust to potential errors in spatial registration between the electro-anatomical map and the anatomical model (since they are typically derived from data coming from different imaging systems).

In another embodiment, the trained system can be used to get a measure of uncertainty of the output. For instance, this can be achieved by applying the network multiple times with slightly perturbed position or values of one or more of the measurement points, and observing the variance of the output. Alternatively, a cascaded model could be used, whereas the first model is trained to predict a physical parameter (e.g., the conduction velocities as described above) and the second model is trained to directly estimate variance (uncertainty) of the output. The first model can be used to generate multiple examples of outputs produced by varying the input. These examples may be used to train the second model to learn the variance of the prediction. One possible implementation of this approach uses a model of the expected noise in the endocardial measurements. For instance, assume that the typical error in the measurements is an error of given amplitude in the measured activation times. In other words, if in one location the measurement is 100 ms, and a 10% measurement error is assumed, then the actual activation time is estimated to be in the range 95-105 ms (milliseconds). Then the training set for the second model is generated by first selecting one set of endocardial measurements, perturbing them randomly according to the noise model, and finally estimating the variance of a variable of interest when the input features are varied. An example of variable of interest is the location of the region with lowest conduction velocity (as defined, e.g., as conduction velocity <100 mm/s (millimeters per second)). For each training sample generated with the first model, the location of the region of lowest conduction velocity can be computed for instance by grouping all vertices with conduction velocity <100 mm/s and then computing the barycenter of their spatial location. The sensitivity of this quantity of interest on the variation of the input features in any of the measurement points could be computed using standard sensitivity analysis tools. The second network could then take as an input the same features as the first model before the noise model is applied and, as the target value, a graph with the same connectivity as the input graph, where each measurement is associated to the estimated sensitivity of the location of the region of lowest conduction velocity with respect to changes of the input features in that node. This approach would enable a system able to suggest where it is safer to acquire the measurements, because the model would associate to each measurement point a sensitivity value explaining how much the uncertainty in the measurement would affect the variable of interest. When used in practice, such a system could indicate that an error in either the position or the value of the endocardial activation time, for instance in AHA (American Hospital Association) sector 3, has limited effect on the location of the region of lowest conduction velocity; or conversely, in some areas extra care should be taken because the value coming from the measurements will affect the estimation drastically.

In another embodiment, the system can be trained to automatically discard measurement points that are inconsistent with the rest of the available input information. Such system can be trained similarly to what described above, with noisy training samples being associated to the same target values. More specifically, the input features are designed so that a set of endocardial measurements are provided, and they are randomly perturbed with mid-intensity noise. In the set of vertices with associated endocardial measurements, all vertices for which the random perturbation is above a certain threshold (e.g., more than 30% of the original value) are labeled as 'discard'. The target values for the network are 2 values for each vertex in the graph: the conduction velocity coming from the computational model (without any noise), and the 'discard' label. This will teach the network to robustly predict the conduction velocity for nodes in which the noise is low intensity, while being able to explicitly label the nodes that had to be discarded because the perturbation would be too much, making them inconsistent with the measured activation times.

The embodiments described herein have the following advantages. Embodiments described herein provide for the robust estimation of local tissue parameters mitigating errors arising from the uncertainty in the spatial sampling and the registration of the contact maps. Embodiments described herein provide for direct estimation of optimal parameters for the incorporated computational model. Consequently, the physics simulation does not need to be carried out repeatedly, reducing the total computation time to a minimum. Embodiments described herein provide for real-time regression of local conductivities, providing a physician with information about the extent of the slow-conduction pathways. It would further allow reasoning about the quality of obtained contact maps. For instance, the network may regress the conductivities with proper uncertainty estimation after every added measurement sample. The uncertainty in prediction over the domain could be visualized and a physician could decide whether additional samples are required and if certain locations require additional care. It would also allow to assess whether enough samples have already been taken, by estimating the information gain coming from additional measurements (e.g., run the system with current measurements, acquire more measurements, run the system again, assess how much the estimated quantities have varied).

A key aspect of the invention is the training of a graph convolutional neural network on a large database of synthetic pairs of input features (sparse contact map, ECG information, and geometry) and local conduction velocities and the smart data augmentation. Using this training data allows the neural network to internalize the underlying physics model and reason about the prevalent conduction velocities. Graph convolutions are hereby a crucial building block since they, in contrast to other machine learning algorithms, are able to learn filters over the neighborhood of a vertex and thus leverage the underlying graph topology. This allows the transport of information throughout the cardiac anatomy, which is necessary to incorporate the contact map. Since the network's output is deterministic it will directly output the local conductivities that are best described by the observed training data, allowing therefore real-time and robust personalization of the computational model.

Claims for methods and systems for training a machine learning based network can be improved with features described or claimed in context of the methods and systems for utilizing a trained machine learning based network, and vice versa.

Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 3:
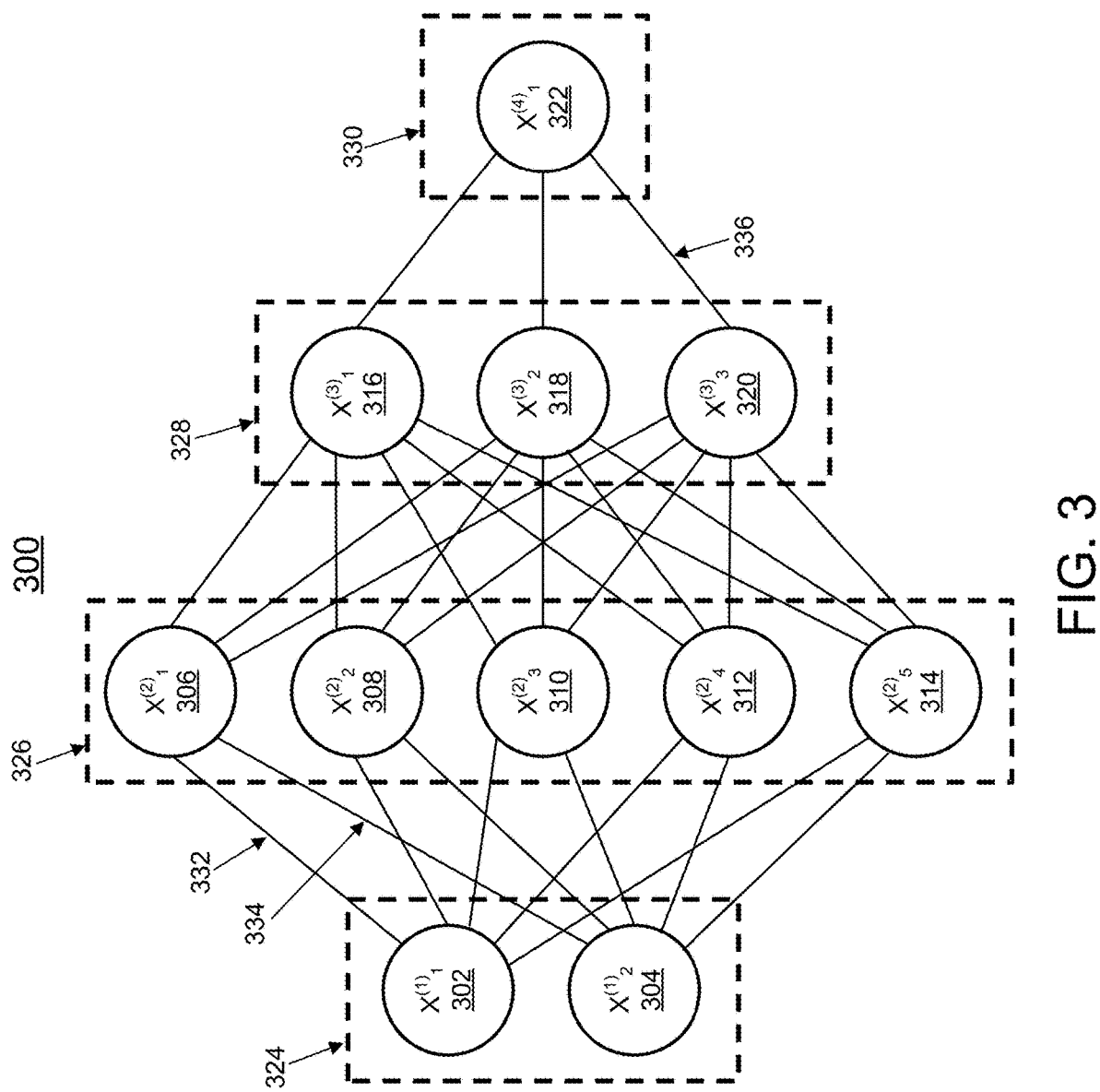
FIG. 3 shows an exemplary artificial neural network.

FIG. 3 shows an embodiment of an artificial neural network 300, in accordance with one or more embodiments. Alternative terms for "artificial neural network" are "neural network", "artificial neural net" or "neural net".

The artificial neural network 300 comprises nodes 302-322 and edges 332, 334, ..., 336 wherein each edge 332, 334, ..., 336 is a directed connection from a first node 302-322 to a second node 302-322. In general, the first node 302-322 and the second node 302-322 are different nodes 302-322, it is also possible that the first node 302-322 and the second node 302-322 are identical. For example, in FIG. 3, the edge 332 is a directed connection from the node 302 to the node 306, and the edge 334 is a directed connection from the node 304 to the node 306. An edge 332, 334, ..., 336 from a first node 302-322 to a second node 302-322 is also denoted as "ingoing edge" for the second node 302-322 and as "outgoing edge" for the first node 302-322.

In this embodiment, the nodes 302-322 of the artificial neural network 300 can be arranged in layers 324-330, wherein the layers can comprise an intrinsic order introduced by the edges 332, 334, ..., 336 between the nodes 302-322. In particular, edges 332, 334, ..., 336 can exist only between neighboring layers of nodes. In the embodiment shown in FIG. 3, there is an input layer 324 comprising only nodes 302 and 304 without an incoming edge, an output layer 330 comprising only node 322 without outgoing edges, and hidden layers 326, 328 in-between the input layer 324 and the output layer 330. In general, the number of hidden layers 326, 328 can be chosen arbitrarily. The number of nodes 302 and 304 within the input layer 324 usually relates to the number of input values of the neural network 300, and the number of nodes 322 within the output layer 330 usually relates to the number of output values of the neural network 300.

In particular, a (real) number can be assigned as a value to every node 302-322 of the neural network 300. Here, $x^{(n)}_i$ denotes the value of the i-th node 302-322 of the n-th layer 324-330. The values of the nodes 302-322 of the input layer 324 are equivalent to the input values of the neural network 300, the value of the node 322 of the output layer 330 is equivalent to the output value of the neural network 300. Furthermore, each edge 332, 334, ..., 336 can comprise a weight being a real number, in particular, the weight is a real number within the interval $[-1, 1]$ or within the interval $[0, 1]$. Here, $w^{(m,n)}_{i,j}$ denotes the weight of the edge between the i-th node 302-322 of the m-th layer 324-330 and the j-th node 302-322 of the n-th layer 324-330. Furthermore, the abbreviation $w^{(n)}_{i,j}$ is defined for the weight $w^{(n,n+1)}_{i,j}$.

In particular, to calculate the output values of the neural network 300, the input values are propagated through the neural network. In particular, the values of the nodes 302-322 of the (n+1)-th layer 324-330 can be calculated based on the values of the nodes 302-322 of the n-th layer 324-330 by $$x_j^{(n+1)} = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions The transfer function is mainly used for normalization purposes.

In particular, the values are propagated layer-wise through the neural network, wherein values of the input layer 324 are given by the input of the neural network 300, wherein values of the first hidden layer 326 can be calculated based on the values of the input layer 324 of the neural network, wherein values of the second hidden layer 328 can be calculated based in the values of the first hidden layer 326, etc.

In order to set the values $w^{(m,n)}_{i,j}$ for the edges, the neural network 300 has to be trained using training data. In particular, training data comprises training input data and training output data (denoted as $t_i$). For a training step, the neural network 300 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 300 (backpropagation algorithm). In particular, the weights are changed according to $$w_{i,j}^{\prime(n)} = w_{i,j}^{(n)} - \gamma \cdot \delta_j^{(n)} \cdot x_i^{(n)}$$

wherein $\gamma$ is a learning rate, and the numbers $\delta^{(n)}_j$ can be recursively calculated as $$\delta_j^{(n)} = (\Sigma_k \delta_k^{(n+1)} \cdot w_{j,k}^{(n+1)}) \cdot f'(\Sigma_i x_i^{(n)} \cdot w_{i,j}^{(n)})$$

based on $\delta^{(n+1)}_j$, if the (n+1)-th layer is not the output layer, and $$\delta_j^{(n)} = (x_k^{(n+1)} - t_j^{(n+1)}) \cdot f'(\Sigma_i x_i^{(n)} \cdot w_{i,j}^{(n)})$$

if the (n+1)-th layer is the output layer 330, wherein f' is the first derivative of the activation function, and $y(n+1)_j$ is the comparison training value for the j-th node of the output layer 330.

Figure 4:
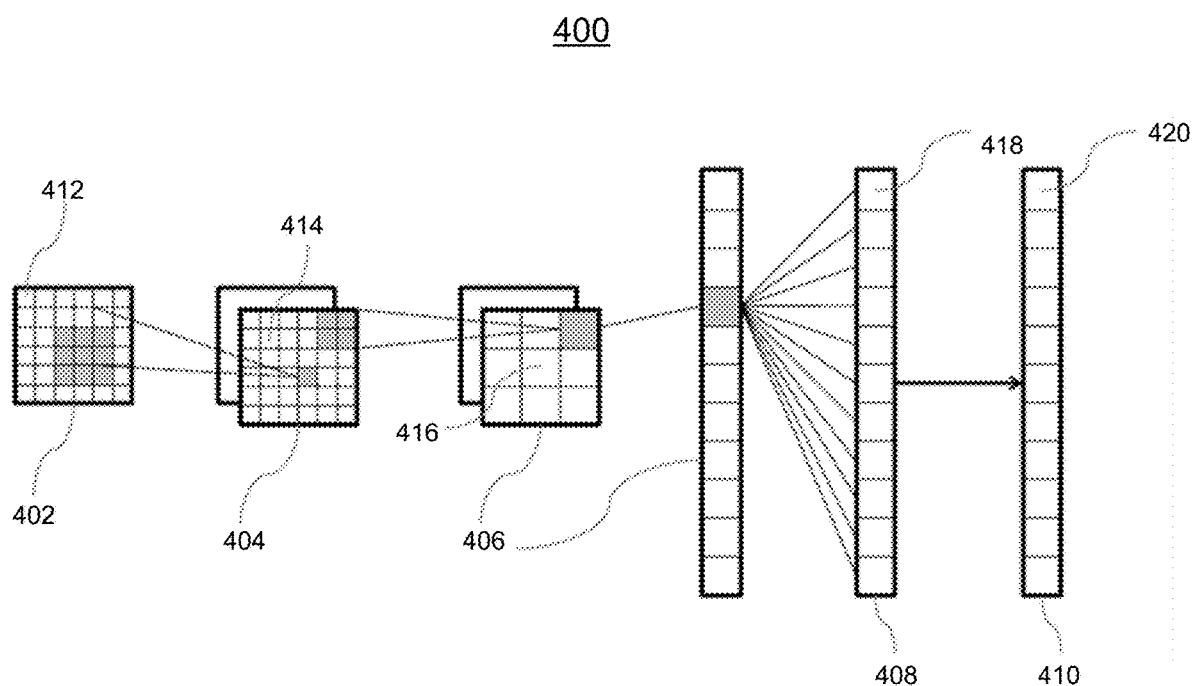
FIG. 4 shows a convolutional neural network.

FIG. 4 shows a convolutional neural network 400, in accordance with one or more embodiments.

In the embodiment shown in FIG. 4, the convolutional neural network comprises 400 an input layer 402, a convolutional layer 404, a pooling layer 406, a fully connected layer 408 1008, and an output layer 410. Alternatively, the convolutional neural network 400 can comprise several convolutional layers 404, several pooling layers 406, and several fully connected layers 408, as well as other types of layers. The order of the layers can be chosen arbitrarily, usually fully connected layers 408 are used as the last layers before the output layer 410.

In particular, within a convolutional neural network 410, the nodes 412-420 of one layer 402-410 can be considered to be arranged as a d-dimensional matrix or as a d-dimensional image. In particular, in the two-dimensional case the value of the node 412-420 indexed with i and j in the n-th layer 402-410 can be denoted as $x^{(n)}_{[i,j]}$. However, the arrangement of the nodes 412-420 of one layer 402-410 does not have an effect on the calculations executed within the convolutional neural network 400 as such, since these are given solely by the structure and the weights of the edges.

In particular, a convolutional layer 404 is characterized by the structure and the weights of the incoming edges forming a convolution operation based on a certain number of kernels. In particular, the structure and the weights of the incoming edges are chosen such that the values $x^{(n)}_k$ of the nodes 414 of the convolutional layer 404 are calculated as a convolution $x^{(n)}_k = K_k * x^{(n-1)}$ based on the values $x^{(n-1)}$ of the nodes 1012 of the preceding layer 402, where the convolution * is defined in the two-dimensional case as $$x_k^{(n)}[i,j]=(K_k * x^{(n-1)})[i,j]=\Sigma_i \Sigma_j K_k[i',j'] \cdot x^{(n-1)}[i-i',j-j'].$$

Here the k-th kernel $K_k$ is a d-dimensional matrix (in this embodiment a two-dimensional matrix), which is usually small compared to the number of nodes 412-418 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 412-420 in the respective layer 402-410. In particular, for a convolutional layer 404, the number of nodes 414 in the convolutional layer is equivalent to the number of nodes 412 in the preceding layer 402 multiplied with the number of kernels.

If the nodes 412 of the preceding layer 402 are arranged as a d-dimensional matrix, using a plurality of kernels can be interpreted as adding a further dimension (denoted as "depth" dimension), so that the nodes 414 of the convolutional layer 414 are arranged as a (d+1)-dimensional matrix. If the nodes 412 of the preceding layer 402 are already arranged as a (d+1)-dimensional matrix comprising a depth dimension, using a plurality of kernels can be interpreted as expanding along the depth dimension, so that the nodes 414 of the convolutional layer 404 are arranged also as a (d+1)-dimensional matrix, wherein the size of the (d+1)-dimensional matrix with respect to the depth dimension is by a factor of the number of kernels larger than in the preceding layer 402.

The advantage of using convolutional layers 404 is that spatially local correlation of the input data can exploited by enforcing a local connectivity pattern between nodes of adjacent layers, in particular by each node being connected to only a small region of the nodes of the preceding layer.

In embodiment shown in FIG. 4, the input layer 402 comprises 36 nodes 412, arranged as a two-dimensional 6×6 matrix. The convolutional layer 404 comprises 72 nodes 414, arranged as two two-dimensional 6×6 matrices, each of the two matrices being the result of a convolution of the values of the input layer with a kernel. Equivalently, the nodes 414 of the convolutional layer 404 can be interpreted as arranges as a three-dimensional 6×6×2 matrix, wherein the last dimension is the depth dimension.

A pooling layer 406 can be characterized by the structure and the weights of the incoming edges and the activation function of its nodes 416 forming a pooling operation based on a non-linear pooling function f. For example, in the two dimensional case the values $x^{(n)}$ of the nodes 416 of the pooling layer 406 can be calculated based on the values $x^{(n-1)}$ of the nodes 414 of the preceding layer 404 as $$x^{(n)}[i,j]=f(x^{(n-1)}[id_1,jd_2], \ldots ,x^{(n-1)}[id_1+d_1-1,jd_2+d_2-1])$$

In other words, by using a pooling layer 406, the number of nodes 414, 416 can be reduced, by replacing a number d1·d2 of neighboring nodes 414 in the preceding layer 404 with a single node 416 being calculated as a function of the values of said number of neighboring nodes in the pooling layer. In particular, the pooling function f can be the max-function, the average or the L2-Norm. In particular, for a pooling layer 406 the weights of the incoming edges are fixed and are not modified by training.

The advantage of using a pooling layer 406 is that the number of nodes 414, 416 and the number of parameters is reduced. This leads to the amount of computation in the network being reduced and to a control of overfitting.

In the embodiment shown in FIG. 4, the pooling layer 406 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 408 can be characterized by the fact that a majority, in particular, all edges between nodes 416 of the previous layer 406 and the nodes 418 of the fully-connected layer 408 are present, and wherein the weight of each of the edges can be adjusted individually.

In this embodiment, the nodes 416 of the preceding layer 406 of the fully-connected layer 408 are displayed both as two-dimensional matrices, and additionally as non-related nodes (indicated as a line of nodes, wherein the number of nodes was reduced for a better presentability). In this embodiment, the number of nodes 418 in the fully connected layer 408 is equal to the number of nodes 416 in the preceding layer 406. Alternatively, the number of nodes 416, 418 can differ.

Furthermore, in this embodiment, the values of the nodes 420 of the output layer 410 are determined by applying the Softmax function onto the values of the nodes 418 of the preceding layer 408. By applying the Softmax function, the sum the values of all nodes 420 of the output layer 410 is 1, and all values of all nodes 420 of the output layer are real numbers between 0 and 1.

A convolutional neural network 400 can also comprise a ReLU (rectified linear units) layer. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer. Examples for rectifying functions are f(x)=max(0,x), the tangent hyperbolics function or the sigmoid function.

In particular, convolutional neural networks 400 can be trained based on the backpropagation algorithm. For preventing overfitting, methods of regularization can be used, e.g. dropout of nodes 412-420, stochastic pooling, use of artificial data, weight decay based on the L1 or the L2 norm, or max norm constraints.

In accordance with one embodiment, the neural network used for classification uses anisotropic 3D kernels to balance resolution and speed and consists of deep dense blocks that gradually aggregate features down to a binary output. The network was trained end-to-end as a classification system using binary cross entropy and uses probabilistic sampling of the training data to adjust for the imbalance in the training dataset labels. A separate validation dataset was used for final model selection before the performance was measured on the testing set. The input 3D tensor size is fixed (2×128×384×384) corresponding to the lung segmentation from the CT data rescaled to a 3×1×1 mm resolution. The first two blocks are anisotropic and consist of convolution (kernels 1×3×3)—batch normalization—LeakyReLU and Max-pooling (kernels 1×2×2, stride 1×2×2). The subsequent five blocks are isotropic with convolution (kernels 3×3×3)—batch normalization—LeakyReLU and Max-pooling (kernels 2×2×2, stride 2×2×2) followed by a final linear classifier with the input 144-dimensional.

Systems, apparatuses, and methods may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows. Certain steps or functions of the methods and workflows may be performed by a server or by another processor in a network-based cloud-computing system. Certain steps or functions of the methods and workflows may be performed by a client computer in a network-based cloud computing system. The steps or functions of the methods and workflows may be performed by a server and/or by a client computer in a network-based cloud computing system, in any combination.

Systems, apparatus, and methods may be implemented using a computer program product tangibly embodied in an information carrier, e.g., in a non-transitory machine-readable storage device, for execution by a programmable processor; and the method and workflow steps may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 5:
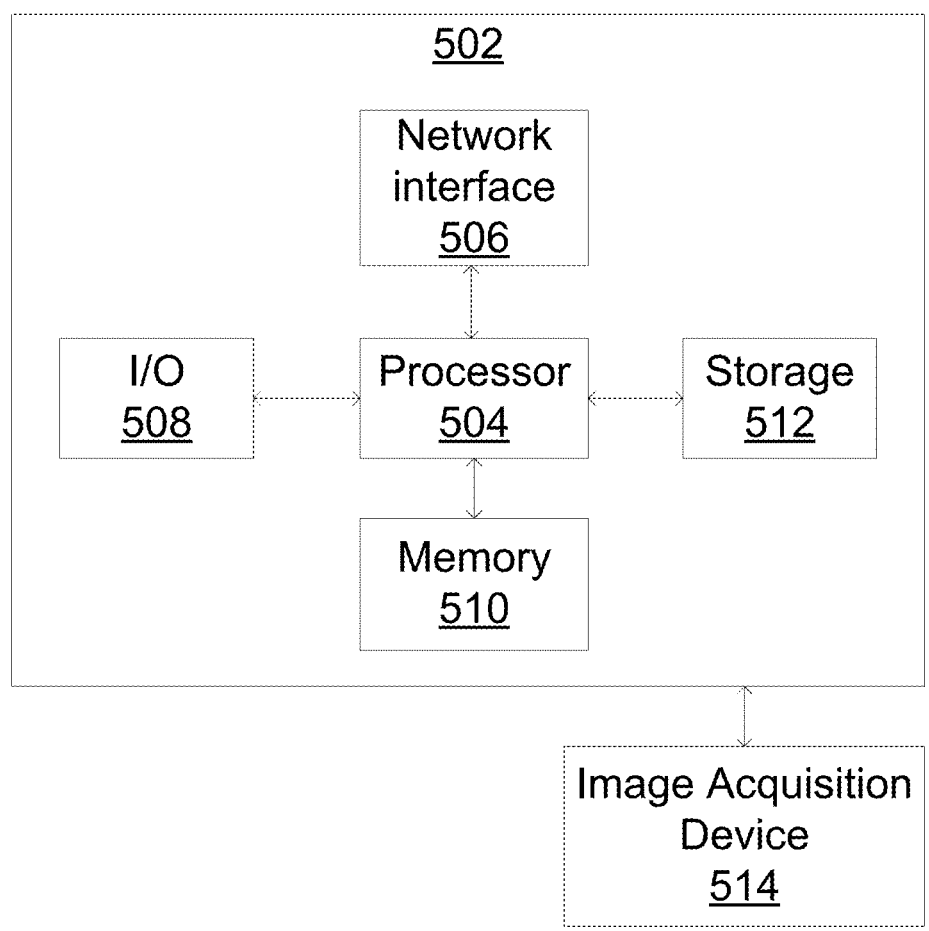
FIG. 5 shows a high-level block diagram of a computer.

A high-level block diagram of an example computer 502 that may be used to implement systems, apparatus, and methods is depicted in FIG. 5. Computer 502 includes a processor 504 operatively coupled to a data storage device 512 and a memory 510. Processor 504 controls the overall operation of computer 502 by executing computer program instructions that define such operations. The computer program instructions may be stored in data storage device 512, or other computer readable medium, and loaded into memory 510 when execution of the computer program instructions is desired. Thus, the method and workflow steps or functions can be defined by the computer program instructions stored in memory 510 and/or data storage device 512 and controlled by processor 504 executing the computer program instructions. For example, the computer program instructions can be implemented as computer executable code programmed by one skilled in the art to perform the method and workflow steps or functions. Accordingly, by executing the computer program instructions, the processor 504 executes the method and workflow steps or functions. Computer 502 may also include one or more network interfaces 506 for communicating with other devices via a network. Computer 502 may also include one or more input/output devices 508 that enable user interaction with computer 502 (e.g., display, keyboard, mouse, speakers, buttons, etc.).

Processor 504 may include both general and special purpose microprocessors, and may be the sole processor or one of multiple processors of computer 502. Processor 504 may include one or more central processing units (CPUs), for example. Processor 504, data storage device 512, and/or memory 510 may include, be supplemented by, or incorporated in, one or more application-specific integrated circuits (ASICs) and/or one or more field programmable gate arrays (FPGAs).

Data storage device 512 and memory 510 each include a tangible non-transitory computer readable storage medium. Data storage device 512, and memory 510, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 508 may include peripherals, such as a printer, scanner, display screen, etc. For example, input/output devices 508 may include a display device such as a cathode ray tube (CRT) or liquid crystal display (LCD) monitor for displaying information to the user, a keyboard, and a pointing device such as a mouse or a trackball by which the user can provide input to computer 502.

An image acquisition device 514 can be connected to the computer 502 to input image data (e.g., medical images) to the computer 502. It is possible to implement the image acquisition device 514 and the computer 502 as one device. It is also possible that the image acquisition device 514 and the computer 502 communicate wirelessly through a network. In a possible embodiment, the computer 502 can be located remotely with respect to the image acquisition device 514.

One skilled in the art will recognize that an implementation of an actual computer or computer system may have other structures and may contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method comprising:
   mapping medical data to an anatomical model of a heart;
   extracting features from the anatomical model mapped with the medical data using one or more feature extraction networks, wherein extracting features from the anatomical model mapped with the medical data using one or more feature extraction networks comprises:
     extracting local features from the anatomical model mapped with the medical data using a graph convolutional neural network;
     extracting global features from the extracted local features using a multilayer perceptron; and
     combining the local features and the global features; and
   determining electrophysiological parameters of the heart based on the extracted features using a prediction network.

2. The method of claim 1, wherein the anatomical model is a tetrahedral mesh of the heart and mapping medical data to an anatomical model of a heart comprises:
   assigning features to edges and vertices of the tetrahedral mesh based on the medical data.

3. The method of claim 1, wherein the medical data comprises data derived from medical imaging data, ECG (electrocardiogram) information, and measurements of electrical activity.

4. The method of claim 1, wherein the electrophysiological parameters comprise conductivities for vertices of the anatomical model.

5. The method of claim 1, further comprising:
   determining a measurement of uncertainty associated with the electrophysiological parameters.

6. The method of claim 5, further comprising:
   suggesting measurement acquisition locations based on the measurement of uncertainty.

7. The method of claim 1, wherein the one or more feature extraction networks are trained using synthetic training data generated by varying parameters of the heart within predetermined value ranges.

8. The method of claim 1, wherein the one or more feature extraction networks are trained using synthetic training data generated by randomly sampling electrophysiological parameters determined using a computational model of the heart.

9. The method of claim 1, further comprising:
   personalizing a computational model of the heart using the electrophysiological parameters.

* * * * *